United States Patent [19]
Pierce et al.

[11] Patent Number: 5,620,454
[45] Date of Patent: Apr. 15, 1997

[54] GUARDED SURGICAL SCALPEL

[75] Inventors: Robert W. Pierce, Wrentham; Neil Jolly, Brighton; Richard V. Kennedy, Hyannis, all of Mass.

[73] Assignee: Becton, Dickinson and Company, Franklin Lakes, N.J.

[21] Appl. No.: 328,996

[22] Filed: Oct. 25, 1994

[51] Int. Cl.⁶ .................................................. A61B 17/32
[52] U.S. Cl. ........................... 606/167; 30/63; 30/162; 30/335
[58] Field of Search .................. 30/267, 151, 163, 30/162, 164, 286, 335; 606/1, 167, 170, 180, 184, 185

[56] References Cited

U.S. PATENT DOCUMENTS

| | | |
|---|---|---|
| 1,914,153 | 6/1933 | Ogden . |
| 2,885,780 | 5/1959 | Campbell . |
| 3,706,106 | 12/1972 | Leopoldi ................................ 7/14.1 |
| 3,905,101 | 9/1975 | Shepard ................................ 30/162 |
| 3,906,626 | 9/1975 | Riuli ..................................... 30/162 |
| 3,943,627 | 3/1976 | Stanley, Jr. ........................... 30/151 |
| 4,091,537 | 5/1978 | Stevenson, Jr ....................... 30/286 |
| 4,393,587 | 7/1983 | Kloosterman ........................ 30/162 |
| 4,414,974 | 11/1983 | Dotson et al. . |
| 4,491,132 | 1/1985 | Aikins . |
| 4,523,379 | 6/1985 | Osterhout et al. ................... 30/151 |
| 4,576,164 | 3/1986 | Richeson . |
| 4,719,915 | 1/1988 | Porat et al. . |
| 4,735,202 | 4/1988 | Williams . |
| 4,757,612 | 7/1988 | Peyrot ................................... 30/151 |
| 4,790,312 | 12/1988 | Capuano, Sr. et al. . |
| 5,071,426 | 12/1991 | Dolgin et al. ........................ 606/167 |
| 5,139,507 | 8/1992 | Dolgin et al. ........................ 606/167 |
| 5,141,517 | 8/1992 | Shutt .................................... 606/167 |
| 5,201,748 | 4/1993 | Newman et al. .................... 606/167 |
| 5,207,696 | 5/1993 | Matwijcow ........................... 30/151 |
| 5,250,063 | 10/1993 | Abidin et al. ........................ 606/167 |
| 5,258,001 | 11/1993 | Corman ................................ 606/167 |
| 5,275,606 | 1/1994 | Abidin et al. ........................ 606/167 |
| 5,292,329 | 3/1994 | Werner ................................. 606/167 |
| 5,292,330 | 3/1994 | Shutt .................................... 606/170 |
| 5,299,357 | 4/1994 | Wonderley et al. ................. 30/339 |
| 5,309,641 | 5/1994 | Wonderley et al. ................. 30/339 |
| 5,330,492 | 7/1994 | Haugen ................................ 606/167 |
| 5,330,493 | 7/1994 | Haining ................................ 606/167 |
| 5,330,494 | 7/1994 | van der Westhuizen ............ 606/167 |
| 5,336,176 | 8/1994 | Yoon ..................................... 604/51 |
| 5,342,379 | 8/1994 | Volinsky ............................... 606/167 |
| 5,411,512 | 5/1995 | Abidin et al. ........................ 606/167 |
| 5,417,704 | 5/1995 | Wonderley ........................... 606/167 |
| 5,423,843 | 6/1995 | Werner ................................. 606/167 |
| 5,496,340 | 3/1996 | Abidin et al. ........................ 606/167 |

FOREIGN PATENT DOCUMENTS 3722899  1/1989  Germany .

*Primary Examiner*—Glenn Dawson
*Attorney, Agent, or Firm*—Eric M. Lee; Arthur D. Dawson

[57] ABSTRACT

This invention relates to an improved guarded surgical scalpel having a movable guard that can be retracted to expose the blade and that can be extended to cover the sharp cutting edge of the blade. The guard is telescopically mounted inside the blade handle and includes a deflectable top wall portion that holds a detent pin. This detent pin engages a slot having upturned ends that is formed in at least one side wall of the blade handle. The detent pin is biased upwardly into the upturned ends to hold the guard in the retracted or extended position.

5 Claims, 4 Drawing Sheets

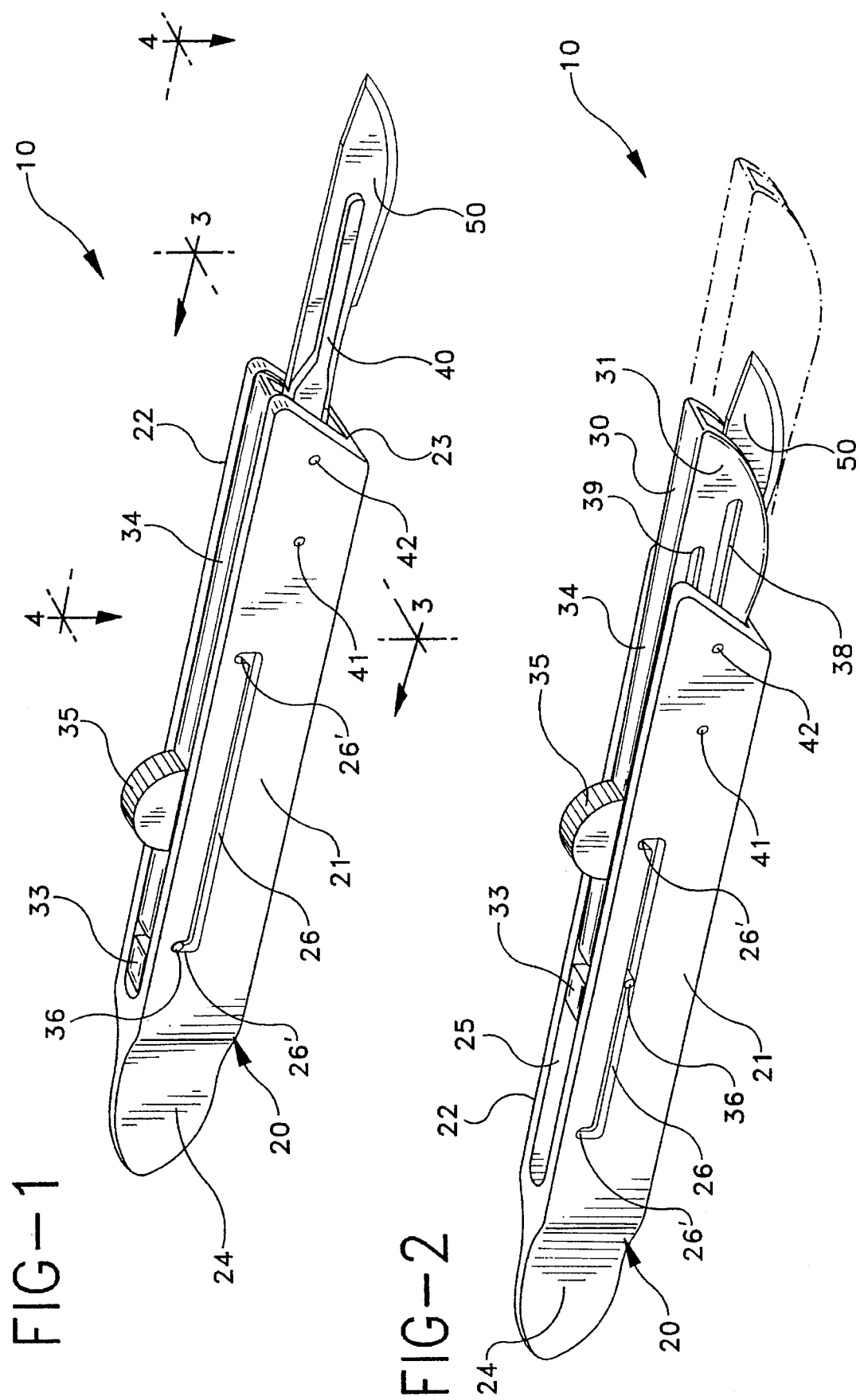

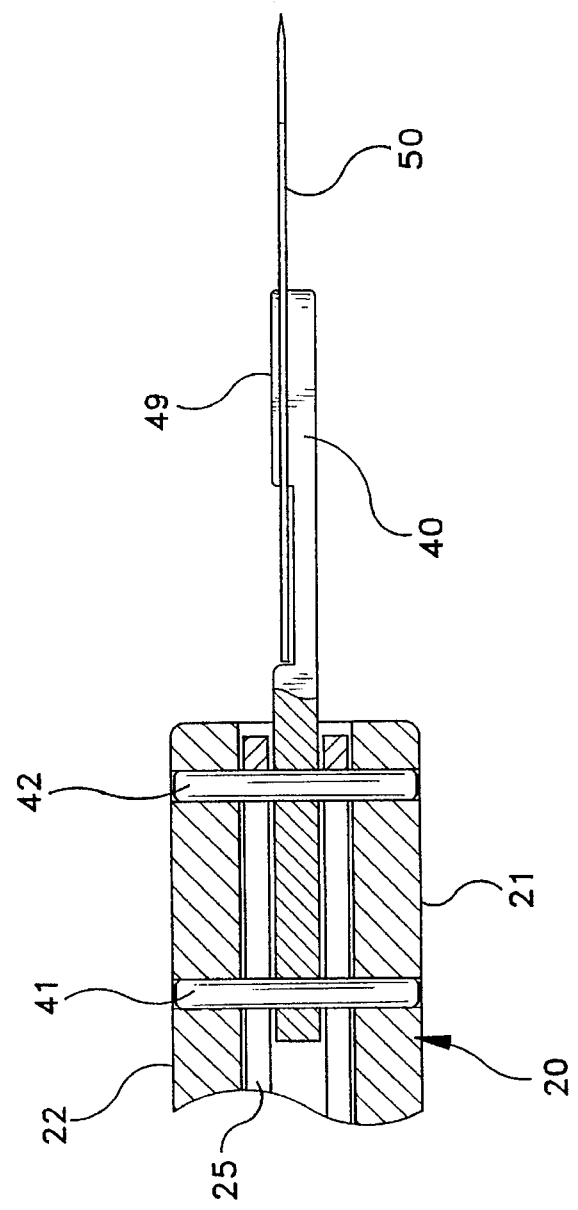
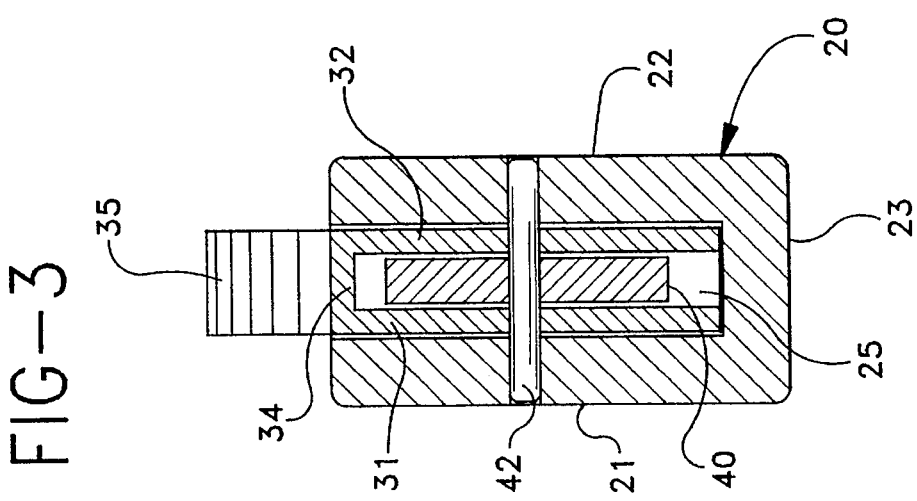

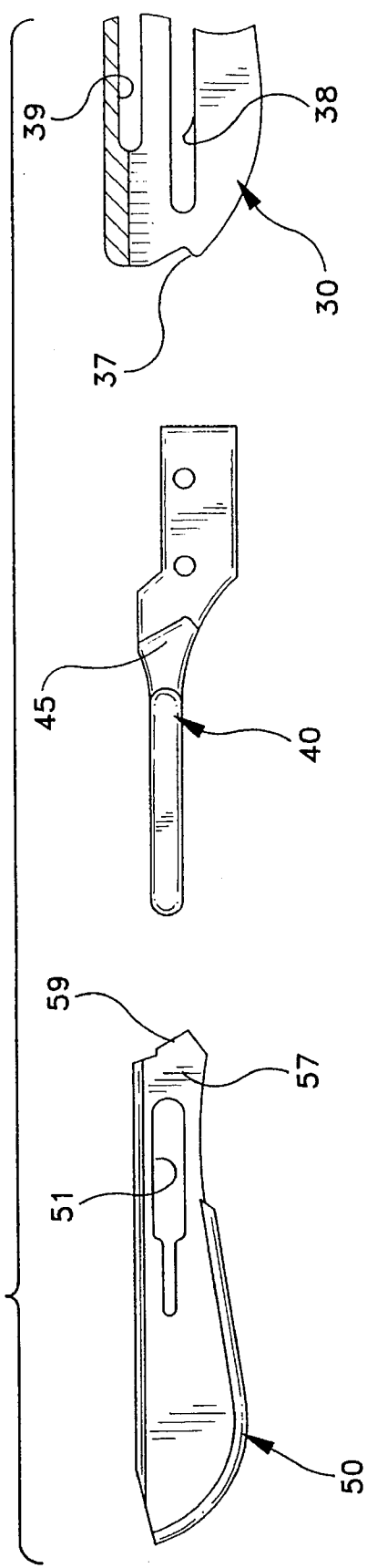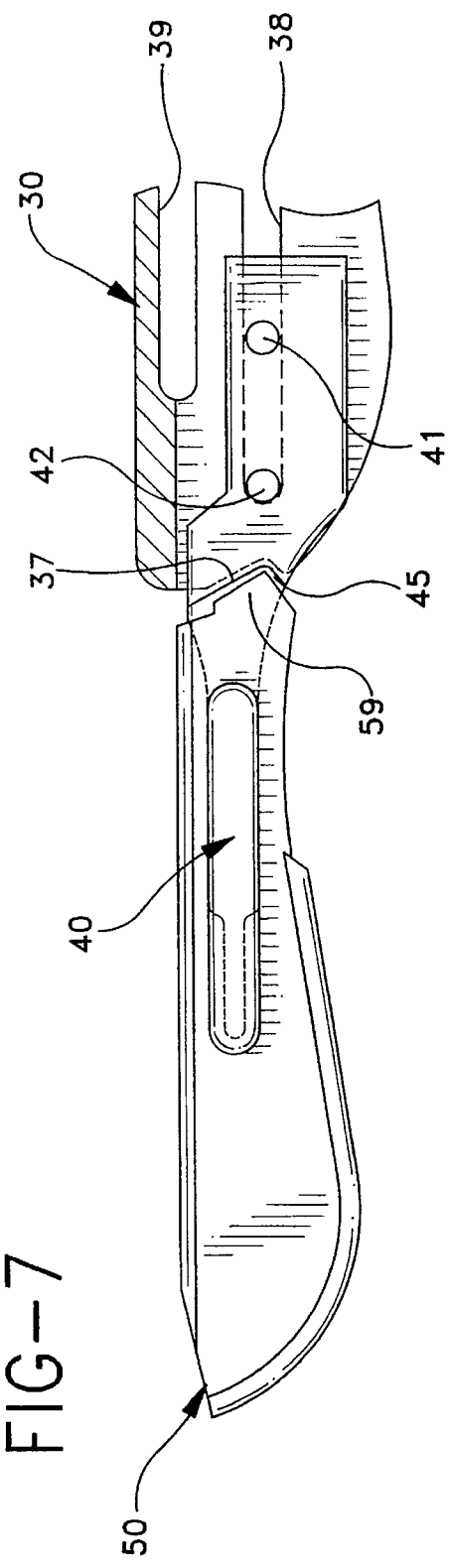

GUARDED SURGICAL SCALPEL

BACKGROUND OF THE INVENTION

The present invention relates to a surgical scalpel and, in particular, to a surgical scalpel having a retractable blade guard to protect against inadvertent nicks or cuts during handling and especially during a surgical procedure in an operating room.

Scalpels are regularly used by surgeons and other health care professionals for making incisions in a patient during an operating procedure. Typically, a nurse hands the scalpel to the surgeon in a predetermined orientation so that the surgeon can grip the scalpel's handle without taking his or her eyes away from the patient. If the nurse accidentally touches the scalpel when it is on the table, does not pay close attention when picking up the scalpel or if the predetermined orientation is not closely followed when the scalpel is transferred to the surgeon, the nurse's or surgeon's hand may be cut or nicked by the blade of the scalpel. The same hazard of being cut or nicked by the blade may be encountered when the surgeon transfers the scalpel back to the nurse.

These nicks or cuts are uncomfortable and distracting. In addition, they may result in blood or body fluid exposure between the patient and the surgeon or other healthcare professional in the operating room. This may lead to the spread of infectious diseases between the patient and the healthcare professional. Concern over this situation has become especially acute because of such diseases as acquired immune deficiency syndrome, i.e. AIDS, and hepatitis.

While surgical gloves aid in reducing the chances of being cut during a surgical procedure, these gloves are not foolproof. And even when two sets of gloves are utilized, full protection is not afforded to the healthcare provider because the scalpel blade can still cut through both sets of gloves. Also, utilizing two sets of gloves reduces finger dexterity by the surgeon and thus is distracting to the surgeon and can interfere with the intended surgical procedure.

In view of the need for a surgical scalpel that can prevent or at least minimize the chances of accidental nicks or cuts during handling, numerous guarded surgical scalpels have been recently designed. Unfortunately, these designs are deficient because they are cumbersome, difficult to use, may cause unwanted shielding or exposure of the scalpel blade prior to the need for such shielding or exposure or may require considerable attention by the user to shield or expose the blade.

SUMMARY OF THE INVENTION

It is therefore an object of the invention to provide a guarded surgical scalpel that prevents or at least minimizes the chances for nicks or cuts during handling.

It is another object of this invention to provide a guarded surgical scalpel that is easy to use and that can be operated by one hand of the user.

It is yet another object of the invention to provide a guarded surgical scalpel that will not allow the blade to be shielded or exposed prior to the need to do so.

It is still another object of this invention to provide a guarded surgical scalpel that can be used without the need for the user to observe the movement of the guard or to place undue attention to its operation.

This invention comprises a guarded surgical scalpel including a handle, a blade connected to the handle, and a guard telescopically mounted within the handle for sliding movement between a retracted position in which the blade is exposed for use and an extended position for covering the sharp cutting edge of the blade. A stop is provided between the guard and the handle for limiting the sliding movement of the guard within the handle. The stop preferably includes at least one pin mounted on the handle transversely thereof and received within a closed longitudinal slot formed in at least one of the side walls of the guard. A unique detent mechanism is provided between the guard and the handle for defining the extended position and the retracted position of the guard on the handle. The detent mechanism comprises a slot with upturned ends formed in at least one sidewall of the handle and a movable top wall formed in the guard to which a pin is connected. This pin engages and rides in the slot formed in the handle. The top wall of the guard, and thus the pin, are biased upwardly so that the pin is captured in the upturned ends of the slot to prevent longitudinal movement of the guard by the application of only a longitudinal force to the guard by the user. The user, however, can move the guard by simply depressing the top wall of the guard to move the pin out of engagement with the upturned ends of the slot.

DESCRIPTION OF THE DRAWINGS

The above and other objects and advantages will be apparent upon consideration of the following drawings and detailed description. The preferred embodiments of the present invention are illustrated in the appended drawings in which like reference numerals refer to like elements and in which:

FIG. 1 is a perspective view of the guarded surgical scalpel of the present invention with the guard in a retracted position to expose the blade;

FIG. 2 is a perspective view of the guarded surgical scalpel of the present invention with the guard in a partially extended position and with the guard shown in phantom in the fully extended position;

FIG. 3 is a cross-sectional view of the guarded surgical scalpel of the present invention taken along line 3—3 of FIG. 1;

FIG. 4 is a cross-sectional view of the guarded surgical scalpel of the present invention taken along line 4—4 of FIG. 1;

FIG. 6 is an exploded side elevation view partially in section showing a portion of the guarded surgical scalpel of the present invention; and FIG. 7 is a side elevation view partially in section showing a portion of the guarded surgical scalpel of the present invention with the guard in a retracted position to expose the blade.

DETAILED DESCRIPTION OF THE INVENTION

Figure 5:
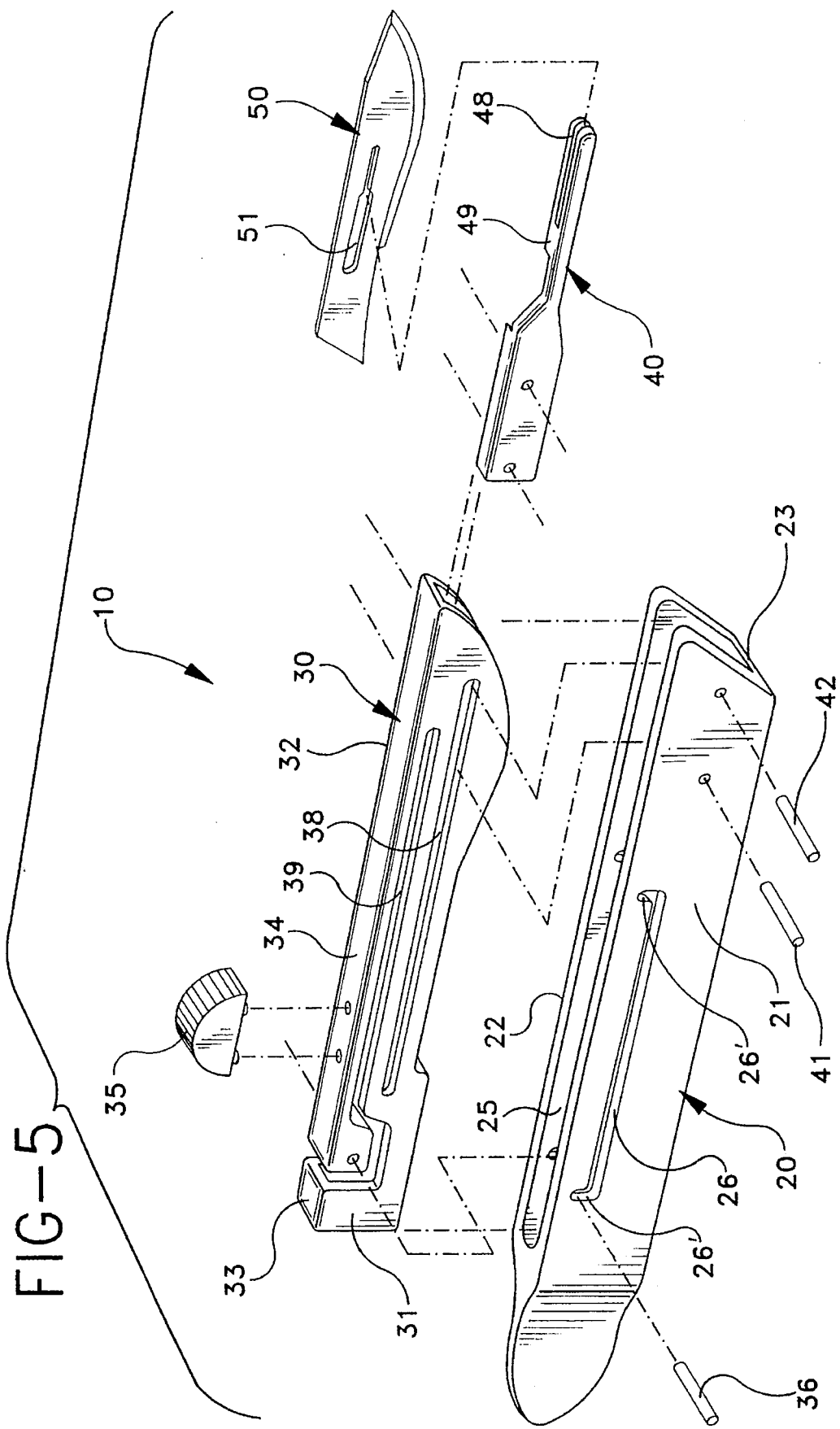
FIG. 5 is an exploded perspective view of the guarded surgical scalpel of the present invention.

The guarded surgical scalpel 10 of the present invention includes a handle 20 having a guard 30 telescopically received within handle 20 for longitudinal sliding movement in handle 20. A blade carrier 40 is mounted on the distal end of handle 20 to allow a blade 50 to be fixedly secured to the distal end of handle 20. Blade carrier 40 is mounted to handle 20 by two transverse pins 41, 42 that extend across the width of handle 20. Pins 41, 42 can be bonded to blade carrier 40 and handle 20 by any conventional means such as orbital riveting, chemical adhesive, ultrasonic bonding or welding. Preferably orbital riveting is used.

Handle 20 has two parallel side walls 21, 22, a bottom wall 23 and a closed proximal end 24. This configuration for handle 20 defines a cavity 25 therein. Proximal end 24 of handle 20 is tapered to a thin portion to provide a blunt dissection tool that can be used during the operating procedure. Side wall 21 of handle 20 preferably defines a slot 26 that is aligned with a slot (not shown) formed in opposing side wall 22. Each slot is generally parallel to the longitudinal axis of handle 20. In addition, the ends of each slot has upturned portions 26' extending away from the main portion of the slot. It is to be noted that the configuration of slot 26 is a mirror image of the configuration of the slot formed in side wall 22. Preferably handle 20 is formed from surgical stainless steel, such as 303 stainless steel. However, hardened stainless steel, such as 410 stainless steel or 420 stainless steel could also be used. In order to have a comfortable and functional product, handle 20 preferably has an overall length of about 4.080 inches, an overall width of about 0.325 inches and an overall height of about 0.510 inches. Preferably the slots each have an overall length of about 1.750 inches.

Guard 30 preferably has two parallel side walls 31, 32 which are connected by a proximal top wall 33 and a distal top wall 34. Preferably side walls 31, 32 have a shape similar to that of a standard surgical scalpel blade. Using this shape for side walls 31, 32 helps the user of guarded surgical scalpel 10 to intuitively understand how to hold and use guarded surgical scalpel 10. Preferably guard 30 is formed from surgical stainless steel, such as 303 stainless steel, but hardened stainless steel, such as 410 stainless steel or 420 stainless steel, can also be used. Side wall 31 defines an upper slot 39 adjacent to distal top wall 34 along substantially the entire length of side wall 31 except for the most distal portion thereof. Side wall 32 also has an upper slot formed therein (not shown) which is aligned with slot 39. It is to be understood that the configuration of slot 39 is a mirror image of the configuration of the upper slot formed in side wall 32. This allows distal top wall 34 to be flexed downwardly in a cantilevered fashion. Depressible distal top wall 34 carries a detent button 35 to facilitate downward flexing of distal top wall 34. A detent pin 36 is located adjacent to the proximal end of distal top wall 34 and may be bonded thereto by press fit, welding or chemical adhesive.

Guard 30 is preferably mounted in cavity 25 of handle 20 for telescopic movement therein and should be dimensioned to allow a tight yet movable fit therein. In order to allow such movement by guard 30, blade carrier 40 is centrally mounted across the distal open end of handle 20 to allow a clearance on either side of blade carrier 40 for side walls 31, 32 of guard 30. This arrangement requires a lower slot 38 to be formed in side wall 31. Side wall 32 also has a lower slot formed therein (not shown) which is aligned with slot 38. It is to be understood that the configuration of lower slot 38 is a mirror image of the configuration of the lower slot formed in side wall 32. Pins 41, 42 engage the ends of the lower slots formed in side walls 31, 32 to limit the sliding movement of guard 30 relative to handle 20. By placing guard 30 within cavity 25, detent pin 36 extends into and rides in the slots formed in side walls 21, 22 of handle 20 and is biased into the upturned portions provided at the ends of these slots when guard 30 is in the fully extended or the fully retracted position. The length of these slots formed in side walls 21, 22 of handle 20 is equal to the amount of travel of guard 30.

When detent pin 36 is located in the upturned portions at the ends of the slots formed in side walls 21, 22 of handle 20, guard 30 is temporarily locked in the extended or retracted position. If the user were to inadvertently apply a longitudinal force to guard 30 or detent button 35 when guard 30 was in one of these positions, guard 30 would not move. In order to move guard 30, a downward force must be applied to distal top wall 34 or detent button 35 to move pin 36 out of engagement with the upturned portions at the ends of the slots formed in side walls 21, 22 of handle 20. Thus, the chances that the user would inadvertently shield or expose blade 50 prior to the need to do so is minimized. In addition, because of the upward bias of distal top wall 34, and thus detent pin 36, the user will automatically know when guard 30 has been moved completely to the extended or retracted position by an audible "click" when pin 36 engages one of the upturned portions at the ends of the slots formed in side walls 21, 22 of handle 20.

In order to allow the user to flex distal top wall 34 downwardly with a comfortable force, the distal portion of the upper slots formed in side walls 31, 32 of guard 30 should begin about 0.705 inches from the distal end of guard 30 when guard 30 is formed from 303 stainless steel. In addition, these upper slots should have a height of about 0.065 inches. These dimensions allow sufficient downward movement of detent pin 36 so it can be moved out of engagement from the upturned portions of the slots formed in side walls 21, 22 of handle 20.

Blade carrier 40 extends forwardly of handle 20 and has a laterally-extending longitudinal rib 49 provided with an external groove 48. Blade carrier 40 is preferably formed from surgical stainless steel, such as 303 stainless steel. However, hardened stainless steel such as 410 stainless steel or 420 stainless steel, could also be used. Blade 50 has a longitudinal slot 51 which cooperates with groove 48 and rib 49 to mount blade 50 on blade carrier 40, thereby mounting blade 50 on handle 20. Blade 50 is relatively thin and very sharp and is "snapped" over rib 49 on blade carrier 40. As shown in FIGS. 6 and 7, blade carrier 40 may include a notch 45 formed therein that mates with another notch 59 formed in the blade tang 57. In addition, sidewalls 31, 32 of guard 30 can each have a notch 37 that matches notch 45. This configuration may be used, if desired, to ensure that only the appropriate blades are used with guarded surgical scalpel 10.

Thus, it is seen that a guarded surgical scalpel is provided that prevents, or at least minimizes, the chances for nicks or cuts during handling, that is easy to use and can be operated by one hand of the user, that will not allow the blade to be shielded or exposed prior to the need to do so, and that can be used without the need for the user to observe the movement of the guard or to place undue attention to its operation.

We claim:

1. A guarded surgical scalpel device, comprising:

a handle having a distal end, a proximal end and a longitudinal axis and two generally parallel side walls and defining a cavity therein, at least one of the side walls defining a slot that is generally parallel to the longitudinal axis of the handle and that has an upturned portion at both ends;

a movable guard disposed in the cavity for longitudinal movement with respect to the handle, the guard having two parallel side walls generally parallel to the two parallel side walls of the handle and a top wall with a distal end and a proximal end that is generally perpendicular to the two parallel side walls of the guard and that is movable in a direction perpendicular to the longitudinal axis of the handle; and a pin mounted on the guard adjacent to the proximal end of the top wall and generally parallel to the top wall and generally perpendicular to the two parallel side walls of the guard so as to extend into the slot whereby movement of the top wall of the guard in a direction perpendicular to the longitudinal axis of the handle moves the pin out of engagement with the upturned portions of the slot.

2. The guarded surgical scalpel device of claim 1 further comprising a button connected to the top wall to facilitate movement of the guard and top wall.

3. The guarded surgical scalpel device of claim 1 further comprising a blade carrier mounted to the distal end of the handle and wherein each of the parallel side walls of the guard extends between one of the parallel side walls of the handle and the blade carrier.

4. The guarded surgical scalpel device of claim 3 further comprising a blade connected to the blade carrier.

5. The guarded surgical scalpel device of claim 4 further comprising a button connected to the top wall to facilitate movement of the guard and top wall.

* * * * *